United States Patent [19]

Yoshida et al.

[11] Patent Number: 4,508,882

[45] Date of Patent: Apr. 2, 1985

[54] BENZOTRIAZOLE COMPOUND AND HOMOPOLYMER OR COPOLYMERS THEREOF

[75] Inventors: Shohei Yoshida, Yokohama, Japan; Otto Vogl, Amherst, Mass.

[73] Assignee: Asahi Glass Company Ltd., Tokyo, Japan

[21] Appl. No.: 457,221

[22] Filed: Jan. 11, 1983

Related U.S. Application Data

[60] Division of Ser. No. 295,545, Aug. 24, 1981, Pat. No. 4,380,643, and a continuation-in-part of Ser. No. 238,090, Feb. 25, 1981, abandoned.

[51] Int. Cl.$^3$ .............................................. C08F 26/06
[52] U.S. Cl. ................................................... 526/259
[58] Field of Search ........................................ 526/259

[56] References Cited

U.S. PATENT DOCUMENTS

| | | | |
|---|---|---|---|
| 3,072,585 | 1/1963 | Milionis et al. | 526/259 |
| 3,197,475 | 7/1965 | Carboni | 526/259 |
| 3,493,539 | 2/1970 | Skoultchi et al. | 526/259 |
| 4,321,396 | 3/1982 | Lorenz et al. | 526/259 |

*Primary Examiner*—Harry Wong, Jr.
*Attorney, Agent, or Firm*—Oblon, Fisher, Spivak, McClelland & Maier

[57] ABSTRACT

Benzotriazole compounds having the formula

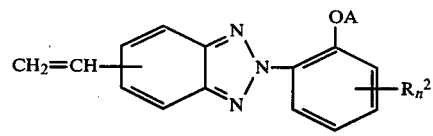

wherein A represents a hydrogen atom or an acetyl group; $R^1$ represents vinyl, ethyl or a haloethyl group; $R^2$ represents a $C_{1-4}$ alkyl group and n is 1 or 2. The $R_2{}^2$ groups need not be identical and a homopolymer or copolymers thereof which are effective as an ultraviolet absorber.

2 Claims, No Drawings

BENZOTRIAZOLE COMPOUND AND HOMOPOLYMER OR COPOLYMERS THEREOF

This application is a continuation-in-part of Ser. No. 238,090, filed Feb. 25, 1981, now abandoned, and is a division of Ser. No. 295,545, filed Aug. 24, 1981, now U.S. Pat. No. 4,380,643.

BACKGROUND OF THE INVENTION

1. Field of the Invention

The present invention relates to the preparation and use of benzotriazole compounds. More particularly, it relates to benzotriazole compounds having vinyl groups which can act as monomers for homo- and copolymerization. It also relates to homopolymer or copolymers of benzotriazole compounds having vinyl groups. The most effective application of these materials is in the ultraviolet protection of plastics, wood and other organic materials.

2. Description of the Prior Art

Plastics used in outdoor are exposed to deleterious solar radiation of a wavelength of 290–400 mm(mµ). The polymer chain or functional group of the polymer exposed to solar radiation absorbs ultraviolet radiation and is excited to a higher energy level, and there is the possibility that certain photochemical reactions are caused. The photochemical reaction could cause degradation of polymer chains, formation of crosslinkage, or the introduction of functional groups in to the plastic material. An ultraviolet absorber is usually incorporated into plastic material in order to protect it from degradation caused by solar radiation. Ultraviolet absorbers absorb most or all of the harmful radiation. Ultraviolet emit them as harmless radiation and also absorbers photoexited energy in the polymer and emit it as harmless energy, which is necessary for stabilizing polymers. Ultraviolet absorbers should be effective for a long time. It is preferable that the ultraviolet absorber does not cause deterioration or discoloration of the plastic material or should not be leached out in contact with a solvent or the other lower molecular weight material. The peak absorption of the ultraviolet absorber should be in the most sensitive wavelength at which the polymer is used. The optimum effect of ultraviolet absorber for protecting plastic materials from harmful effect of solar radiation should be considered from the point of view of photochemical properties and other functions. For example, it is not enough to have only a high absorbancy index (extinction coefficient) in an ultraviolet region and nondestructive emission of absorbed energy. In general, the most important factor for the selection of ultraviolet absorbers is not only the photochemical property. It is necessary for the ultraviolet absorber to have desired photochemical properties, for example, to have a high absorbancy index in the wavelength region of 300–350 nm. The ultraviolet absorber should be stable and not color or decompose on exposure solar radiation. In order to be not colored the ultraviolet absorber preferably has low absorbancy in the long wavelength region. If the ultraviolet absorber should be considered for preventing sun-burn it should be effective for a long time. The cosmetic ultraviolet absorbers should have low toxicity without any allergic effect. Moreover, the tissue toxicity in penetration into skin should be also low. For example, low molecular compounds such as β-aminobenzoic acid derivatives and salicylic acid derivatives are not satisfactory. The effect of polymeric ultraviolet absorbers depends upon the molecular weight and its volatility. Polymeric ultraviolet absorbers having low volatility and low leachability are preferable. In 2-hydroxy-4-alkoxybenzophenones, this has been attempted but not achieved satisfactorily by having a long alkoxy group, which also improves the compatibility with the polymer. Especially with hydrocarbon polymers compatibility is increased and volatility is decreased by the increase of the length of side chain groups, for example, to the length of the dodecyloxy group.

Polymeric ultraviolet absorbers have been known in prior arts. 2-Hydroxy-4-methacryloxybenzophenone is obtained by reacting 2,4-dihydroxybenzophenone with methacrylic acid derivatives. Other derivatives have been obtained from 2,4-dihydroxybenzophenone. For example, the allyl ether of 2,2',4-trihydroxybenzophenone and 4-chloromethylstyrene. Allyloxy, acrylamino, methacrylamino, vinylsulfoxy and vinyloxy derivatives of 2-(2-hydroxy-5-phenyl)benzotriazole have also been described and their copolymerization with such a comonomer as styrene, acrylonitrile or butadiene are claimed.

SUMMARY OF THE INVENTION

It is an object of the present invention to provide benzotriazole compounds as a source for polymeric ultraviolet absorbers especially 2-hydroxy benzotriazole compounds having a polymerizable unsaturated group on the phenyl ring of the benzotriazole group, and the intermediates thereof.

Another object of the present invention is to provide 2-hydroxyphenyl benzotriazole compounds having a polymerizable unsaturated groups on the phenyl ring of the benzotriazole group which can be homopolymerized or copolymerized with a comonomer to obtain polymeric ultraviolet absorbers.

The benzotriazole compounds of the present invention have the following formula

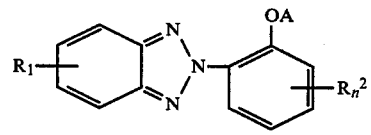

wherein A represents a hydrogen atom, or a acetyl group; $R^1$ represents a vinyl or haloethyl group or ethyl group; $R^2$ represents a $C_{1-4}$ alkyl group and n is 1 or 2, $R_2{}^2$ need not be the same group in a formula.

In the formula, $R^1$ is preferably at the 5-position, but may be at 4-position. Among the compounds the most effective compounds have a vinyl group as the $R_1$ group. The compounds having ethyl or haloethyl group as $R^1$ are effective as the intermediate for the synthesis of compounds having a vinyl groups as $R^1$. The haloethyl group is preferably the 1-haloethyl having Cl, Br or I especially Br as the halogen atom.

DETAILED DESCRIPTION OF THE PREFERRED EMBODIMENTS

In the present invention, the most effective compounds as the source for polymeric ultraviolet absorbers useful for a number of applications are 2(2-hydroxy-5-methylphenyl)5-vinyl-2H-benzotriazole, and 2(2-acetoxyl-5-methylphenyl)-5-vinyl-2H-benzotriazole.

The characteristics of the compounds of the present invention are excellent optical properties with a broad absorption having the highest intensity in ultraviolet region and low absorbancy in the visible region with excellent thermal and other types of stabilities. The styrene type compounds having vinyl group as a polymerizable group on the benzotriazole group of 2(2-hydroxyphenyl)2H-benzotriazole have such characteristics. The compounds having an ethyl or a haloethyl group instead of a vinyl group are intermediates and can be converted into the compounds with the vinyl group.

The vinyl compounds of the present invention can be homopolymerized or copolymerized with a comonomer having a polymerizable unsaturated group to produce the polymeric ultraviolet absorbers. The compounds having vinyl group of the present invention are easily purified and have high polymerizability for homopolymer or copolymer formation, they have excellent characteristics in comparison with other known polymeric ultraviolet absorbers. The vinyl group on the benzotriazole group in comparison with the vinyl group substitution on 2-hydroxyphenyl group is important to provide more useful monomers which have different copolymerization characteristics by its more electron deficient properties. It is also important to have the possibility of utilizing two $R^2$ groups in order to improve the ultraviolet absorbing properties or to improve the stabilities of the hydroxy groups, and in addition to minimize the coloring of the compounds, that is, polymers with other metal complex additive, or possible oxidative degradation. Therefore, the polymeric ultraviolet absorbers having excellent balanced characteristics of the ultraviolet absorbance and other physical properties and functions can be obtained.

The preferable process for producting the compounds of the present invention will be illustrated.

As the sources, ethyl-o-nitroaniline and an alkylphenol are used. It is better to have the 4-substituted alkyl phenol to obtain the 2(2-hydroxyphenyl)2H-benzotriazole structure in a high yield, at least one o-position of the alkyl phenol must be unsubstituted. The ethyl substitution in o-nitroaniline may be in the 3- or 4-position, usually 4-ethyl-o-nitroaniline is more easily obtained. Ethyl-o-nitroaniline is diazotizated with a nitrite and then alkylphenol is added to perform the condensation reaction to an azodye and the product is reduced to obtain 2(2-hydroxyalkylphenyl)ethyl-2H-benzotriazole. The process for producing the conventional benzotriazole ultraviolet absorbers can be applied. In the next steps the ethyl group of the compound is converted into the vinyl group. For example, the hydroxy group is protected by acetylation before the bromination of the ethyl group with N-bromosuccinimide. The bromoethyl group is further converted into the vinyl group by dehydrobromination, and then, the acetoxy group is removed by hydrolysis to the vinyl compound of the present invention.

The process for producing the vinyl compound of the present invention is not limited to the above-mentioned process. As the optimum process, 2-(2-hydroxy-5-methylphenyl)5-ethyl-2H-benzotriazole is produced by the conventional process and then the ethyl group is converted into the vinyl group.

The compounds having vinyl group of the present invention (hereinafter referred to as benzotriazole monomer) have the vinyl group as the polymerizable unsaturated group. Therefore, the benzotriazole monomer can be homopolymerized or copolymerized with a comonomer in the presence of a polymerization initiator, azoinitiators such as azobisisobutyronitrile or peroxides such as BPO. In the copolymerization the type of comonomer is not critical, it can be any monomer having a polymerizable unsaturated group such as styrene, acrylonitrile, methacrylic esters, acrylic esters, butadiene, isoprene, vinyl chloride, chloroprene or other vinyl monomers. Compared to compounds with the vinyl group in the phenol ring, the vinyl group on the benzotriazole ring make the incorporation of the monomer of the present invention easier to the olefinic copolymer such as styrene, acrylic ester copolymer. It is possible to understand the character by its relatively active radical character. It is also possible to use polyvinyl compounds such as divinyl monomer and vinylidene monomers and other compounds having $\alpha,\beta$-unsaturated group. Usual grafting polymerization on the polymer in bulk or solution can provide the polymeric ultraviolet absorbers.

The homopolymers of the benzotriazole monomer or the copolymer having relatively high contents of benzotriazole monomer unit can be used as addition type ultraviolet absorbers for synthetic resins and other products. The copolymers having relatively low content of benzotriazole monomer units are effective as polymers having ultraviolet absorbancy. The benzotriazole monomer is used as a reactive type ultraviolet absorber. In the latter case, the ratio of the benzotriazole unit to polymer can be low. For example, the copolymer having ultraviolet absorbancy can be obtained by incorporating only 0.01 wt.% of the benzotriazole monomer unit. The ratio of the benzotriazole monomer to the total monomer in the copolymerization can be more than 1 wt.% to impact the ultraviolet absorbancy to the polymer. The maximum ratio is not critical and homopolymers of the benzotriazole monomer are also effective. In view of economical aspects, the upper limit of the ratio of the benzotriazole monomer to the total monomer is about 70 wt.% in the case of the relative ultraviolet absorber. The copolymer having relatively high content of the benzotriazole monomer unit or the homopolymers of the benzotriazole monomer can be used as the addition type ultraviolet absorbers. For example, the polymeric ultraviolet absorber can be incorporated into various synthetic resins to prepare synthetic resins having ultraviolet absorbancy. It also can be used to incorporate it by coating or surface grafting. The amount of the benzotriazole monomer unit in the copolymer as the addition type ultraviolet absorber depends upon the amount of the copolymer in the product, or the amount of the copolymer in the product depends on the content of the benzotriazole monomer unit in the copolymer. Therefore, the actual amount of the benzotriazole monomer unit in the copolymer is needed to impart desired ultraviolet absorbancy into the product. The content of the benzotriazole monomer unit in the product is usually more than 0.01 wt.%.

The present invention also relates to the homopolymer or copolymer of the benzotriazole monomer. The copolymer obtained by copolymerizing 0.01 to 70 wt.% of the benzotriazole monomer with a comonomer are especially preferably used in various application requiring ultraviolet absorbancy. The copolymer can be a random copolymer but also can be a graft copolymer obtained by grafting the benzotriazole monomer on to a copolymerizable polymer.

The benzotriazole monomer can be used as a reactive ultraviolet absorber in polymerizable composition which is to be cured for example as the reactive component for curable polymerizable resin composition, such as unsaturated polyester resin compositions. When the curable polymerizable resin composition is polymerized, the benzotriazole monomer is also copolymerized with the polymerizable component by random or graft copolymerization to obtain a cured product having ultraviolet absorbancy.

When the benzotriazole monomer is used as the copolymerizable component of a polymer, the stability of the polymer to ultraviolet rays can be improved to obtain a plastic having excellent weathering resistance. The homopolymer or the copolymer of the present invention can be incorporated into the other plastic or can be used for coating the plastic instead of the conventional ultraviolet absorber to improve the weathering resistance of the plastic. The benzotriazole monomer itself or the oligomer of the monomer of the present invention can be used for various purpose. The benzotriazole, or the homopolymer or copolymers can be also used for various applications, for examples, as a component or additive for synthetic fibers, for a surface processing agent or dying agent for fibers, for a component for coatings or paints or impregnating wood or as a component for cosmetics or sun screen lotion. It is also possible to use them as medical substrates which should have high weathering resistance. The uses are not critical. In these uses, it is possible in many cases to combine it with an antioxidant.

The present invention will be further illustrated by certain examples, which are provided for purposes of illustration only and are not intended to be limiting the present invention.

EXAMPLE 1

Preparation of 2(2-acetoxy-5-methylphenyl)5-ethyl-2H-benzotriazole

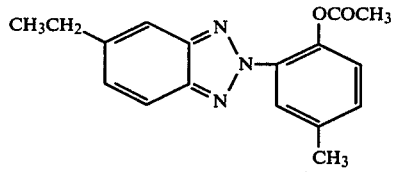

3-Nitro-4-aminoethylbenzene (55.4 g, 0.4 mole), dispersed in 160 ml of water and 150 ml of conc. hydrochloric acid was diazotized by the dropwise addition over a period of one hour at 0° to 5° C. of a solution of sodium nitrite (30 g, 0.45 mole) in water (100 ml). The diazonium salt solution was added from a dropping funnel over a period of 30 min. at 15° C. to a stirred solution of p-cresol (43 g, 43.3 g, 0.4 mole), sodium hydroxide (16 g, 0.4 mole), sodium carbonate (120 g, 1.13 mole) and 600 ml of water, which had been placed in a two liter beaker.

The azo compound separated as a dark red crystalline solid after continued stirring of the reaction mixture for several hours, it was dissolved in aqueous 2N sodium hydroxide (400 ml, 0.8 mole) solution, and this mixture, in a two liter beaker equipped with a mechanical stirrer, was placed in a water bath. Zinc powder (120 g, 1.84 mole) was added to the stirred solution which resulted in an exothermic reaction; additional 25% aqueous sodium hydroxide (200 ml) was added over a period of 3 hours. After the first hour the color of the reaction had changed from red to green; the reaction was completed at 70° C. The suspension was cooled to room temperature and allowed to settle, the supernatant liquid decanted, the remaining suspension filtered and the filter cake washed with chloroform. The filtrate was acidified with 6-N aqueous hydrochloric acid solution, extracted with chloroform and the organic layer thoroughly washed and dried over anhydrous magnesium sulfate. After removing the solvent under reduced pressure, a viscous dark brown oil (crude 2(2-hydroxy-5-methylphenyl)5-ethyl-2H-benzotriazole) was obtained in 80% yield (95 g). This product was immediately acetylated with acetic anhydride (150 g) and 1 g of conc. sulfuric acid as a catalyst followed by removal of acetic acid by distillation under reduced pressure. 2(2-Acetoxy-5-methylphenyl)5-ethyl-2H-benzotriazole was purified by distillation (180° C., 0.05 mmHg). The yield was 49%. The product was recrystallized from n-pentane and had the following properties.

Melting point: 96°–97° C.

| | Elemental analysis: | | |
|---|---|---|---|
| | C | H | N |
| Calculated: | 69.14% | 5.80% | 14.23% |
| Found: | 69.38% | 5.97% | 14.53% |

NMR spectrum: Table 1.

EXAMPLE 2

Preparation of 2(2-hydroxy-5-methylphenyl)5-ethyl-2H-benzotriazole

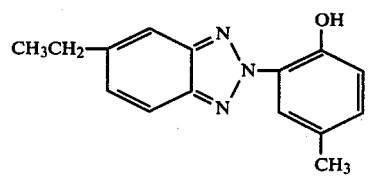

Pure 2(2-hydroxy-5-methylphenyl)-5-ethyl-2H-benzotriazole was obtained by the hydrolysis of 2(2-acetoxy-5-methylphenyl)5-ethyl-2H-benzotriazole. A solution of 2(2-acetoxy-5-methylphenyl)5-ethyl-2H-benzotriazole (5.9 g, 0.02 mole) and 10 ml of ethanol was poured into a solution of sodium hydroxide (2.0 g, 0.05 mole). The resulting fine dispersion was heated to 80° C. for 3 hours. After cooling to room temperature, the homogeneous solution was acidified with 1N aqueous hydrochloric acid solution and the solid precipitate was extracted with carbon tetrachloride. The solution was chromatographed and the eluate concentrated under reduced pressure. The residue was recrystallized from n-hexane by cooling to −78° C. White needles were obtained which were collected by filtration, washed with cold n-hexane and dried. 2.7 g (54% yield) of 2(2-hydroxy-5-methylphenyl)5-ethyl-2H-benzotriazole was obtained, which had following properties.

Melting point: 91°–91.5° C.

| | Elemental analysis: | | |
|---|---|---|---|
| | C | H | N |
| Calculated: | 71.13% | 5.97% | 16.59% |
| Found: | 71.32% | 5.83% | 16.89% |

NMR spectrum: Table 1.

EXAMPLE 3

Preparation of 2(2-acetoxy-5-methylphenyl)5(1-bromoethyl-2H-benzotriazole

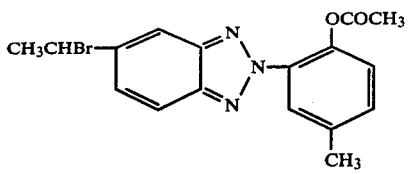

In a 500 ml three necked flask equipped with a mechanical stirrer and a refluxing condenser was placed pure crystalline 2(2-acetoxy-5-methylphenyl)5-ethyl-2H-benzotriazole (29.5 g, 0.1 mole), NBS (18.9 g, 0.105 mole) and carbon tetrachloride (165 ml). The mixture was heated to reflux and AIBN (0.33 g, 2 mole) was added as the catalyst. After 1 hour of reaction the $^1$H NMR spectrum of the reaction mixture showed the disappearance of the starting materials of the methylene proton absorption and the appearance of methine proton absorption of the brominated product. The mixture was filtered to remove succinimide and excess NBS, the carbon tetrachloride solution was washed with 5% aqueous solution of sodium bicarbonate and water, concentrated and dissolved in chloroform (100 ml), which produced a small amount of solid, which was removed and the filtrate again concentrated under reduced pressure, chromatographed, brought to dryness and recrystallized from n-hexane; white needles obtained in a yield of 67% (25.1 g), had the following properties.

Melting point: 58.5°–59.5° C.

| | Elemental analysis: | | | |
|---|---|---|---|---|
| | C | H | N | Br |
| Calculated: | 54.57% | 4.29% | 11.23% | 21.36% |
| Found: | 54.54% | 4.47% | 11.17% | 21.56% |

NMR spectrum: Table 1.

EXAMPLE 4

Preparation of 2(2-acetoxy-5-methylphenyl)5-vinyl-2H-benzotriazole

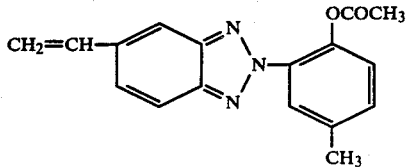

In a 500 ml three neck flask which was fitted with a mechanical stirrer and a reflux condenser, 2(2-acetoxy-5-methylphenyl)5(1-bromoethyl)2H-benzotriazole (30 g, 0.08 mole), triethylamine (41 g, 0.40 mole), acetonitrile (120 g) and picric acid (0.1 g, 0.4 mmole) were dissolved and rapidly heated to reflux by dipping the flask into a heated oil bath. The progress of the reaction was followed by $^1$H NMR measurements of samples taken from the reaction mixture. After 2 hours the methine proton resonance of the starting material had disappeared and the vinyl protons had appeared at 5–6 ppm.

The reaction mixture was cooled, diluted with carbon tetrachloride (200 ml) and stirred with a 6N aqueous hydrochloric acid solution at 0° to 5° C. The organic phase was separated and washed three times with 2N aqueous hydrochloric acid solution and water and brought to dryness. The residue was dissolved in dichloromethane (50 ml) and the solution poured into 500 ml of n-hexane which resulted in the precipitation of a small amount of polymeric material which was removed by filtration.

The solution was concentrated under reduced pressure and a pale brown viscous liquid was obtained. The oily residue deposited yellow crystals. Further recrystallizations gave white transparent crystals in 25% yield. The resulting product had the following properties.

Melting point: 69°–73° C.

| | Elemental analysis: | | |
|---|---|---|---|
| | C | H | N |
| Calculated: | 69.61% | 5.15% | 14.33% |
| Found: | 69.64% | 5.27% | 14.35% |

NMR spectrum: Table 1.

EXAMPLE 5

Preparation of 2(2-hydroxy-5-methylphenyl)5-vinyl-2H-benzotriazole

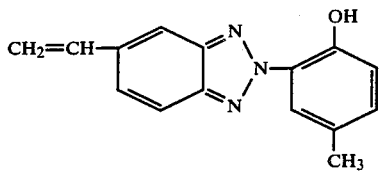

In a 200 ml flask equipped with a reflux condenser and a mechanical stirrer were placed 2(2-acetoxy-5-methylphenyl)5-vinyl-2H-benzotriazole (7.2 g, 24.5 mmole), a 20% solution of sodium hydrogencarbonate (4.2 g), methanol (110 g) and picric acid (0.01 g). The mixture was heated and kept for 1.5 hours at reflux temperature. The clear, yellow solution was cooled to room temperature, filtered and acidified slowly at 0° to 50° C. with 1N aqueous hydrochloric acid solution. The precipitate was dissolved in chloroform (100 ml), and the organic layer was concentrated. Several precipitations of the chloroform or a dichloromethane solution into methanol were sometimes necessary to remove some insoluble material. The vinyl compound was finally crystallized from methanol/water, dried at 0.05 mm, and gave 3.4 g (55%) yield. Which had the following properties.

Melting point: 103°–105° C.

| | Elemental analysis: | | |
|---|---|---|---|
| | C | H | N |
| Calculated: | 71.70% | 5.21% | 16.72% |
| Found: | 70.74% | 4.92% | 16.43% |

NMR spectrum: Table 1.

REFERENCES

The following references are preparations of homopolymers or copolymers of 2(2-hydroxy-5-methylphenyl)-5-vinyl-2H-benzotriazoles.

REFERENCE 1

Preparation of Homopolymer

Into a 5 ml glass tube, 2(2-hydroxy-5-methylphenyl)5-vinyl-2H-benzotriazole (0.75 g, 3 mmole), toluene (1.80 ml) and azobisisobutylonitrile (2.5 mg, 0.015 mmole) were charged. The homogeneous mixture was degassed by three freeze-thaw cycles with nitrogen sweep, sealed at 0.005 mmHg and the tube was placed in a constant temperature bath of 50° C. for 14 days.

After the polymerization, the content was taken out from the tube and dissolved in 5 ml chloroform and precipitated into 50 ml methanol. The resulting precipitate was collected by filtration and dried under reduced pressure for a few days. A 76 wt.% yield (0.39 g) was obtained with a $\eta_{inh}$ viscosity of 0.05 dl/g (0.5 g/dl solution of chloroform at 30° C.).

REFERENCE 2

Copolymerization with Methyl Methacrylate

In a 5 ml polymerization tube were placed 2(2-acetoxy-5-methylphenyl)5-vinyl-2H-benzotriazole (0.40 g, 1.6 mmole), MMA (0.91 g, 9.1 mmole), AIBN (3.3 mg, 0.02 mmole), and toluene (1.3 g). The homogeneous mixture was degassed by three freeze-thaw cycles with a nitrogen sweep, sealed at 0.005 mmHg and the tube was placed in a constant temperature bath of 50° C. After 8 days it was opened, the viscous contents dissolved in 5 ml of dichloromethane and filtered. The solution was poured into 400 ml of methanol, the solid collected by filtration, washed with methanol (50 ml) and dried under reduced pressure for a few days; a 30 wt.% yield (0.39 g) of copolymer with a $\eta_{inh}$ viscosity of 0.1 dL/g (0.5 g/dl solution of chloroform at 30° C.) was obtained. The copolymer composition was about 16 mole % as judged by NMR spectroscopy where the aliphatic protons adjacent to the ester oxygen of the acrylate were compared to the aromatic protons.

REFERENCE 3

Copolymerization with Styrene

In a 3 ml polymerization tube were placed 2(2-hydroxy-5-methylphenyl)5-vinyl-2H-benzotriazole (0.25 g, 1 mmole), acetone (0.20 ml) styrene (0.59 g, 5.7 ml) and azobisisobutyronitrile (5.5 mg, 0.033 mmole). The homogenous mixture were degassed by three freeze-thaw cycles with nitrogen sweep, sealed at 0.005 mmHg and the tube was placed in a constant temperature bath of 50° C. for 2 weeks.

After the polymerization was judged complete the content of the tube was dissolved in 10 ml of chloroform and the polymer precipitated into 100 ml of methanol. The resulting precipitate was collected by filtration and dried under reduced pressure for a few days. A yield of 42 wt.% (0.35 g) of copolymer was obtained with an $\eta_{inh}$ viscosity of 0.07 dL/g (0.5 g/dl solution of chloroform at 30° C.). The copolymer composition was about 15 mole % of benzotriazole monomer as judged by elemental analysis for nitrogen.

REFERENCE 4

Copolymerization with Butyl Acrylate

In a 5 ml polymerization tube were placed 2(2hydroxy-5-methylphenyl)5-vinyl-2H-benzotriazole (0.4 g, 1.6 mmole), toluene (1.56 ml), butyl acrylate (1.16 g, 9.1 mmole) and azobisisobutyronitrile (3.5 mg, 0.021 mmole). The homogenous mixture was degassed by three freeze-thaw cycles with nitrogen sweep, sealed at 0.005 mmHg and the tube was placed in a constant temperature bath of 50° C. for 11 days.

After the polymerization was judged complete the content of the tube was dissolved in 5 ml of chloroform and precipitated into 50 ml methanol. The resulting viscous precipitate was taken out by a decantation, dissolved in 2 ml of benzene and dried in a vacuum under freezing point of the solution. A 9 wt.% of yield (0.14 g) of the copolymer was obtained with an inherent viscosity $\eta_{inh}$ of 0.10 dL/g (0.5 g/dl solution of chloroform at 30° C.). The copolymer composition was ap. 22 mole % of benzotriazole monomer as judged by nitrogen analysis of the copolymer.

TABLE 1

Chemical Shift Data of $^1$H NMR Spectra of 2(2-Hydroxy-5-Methyl)-5-Vinyl-2H—Benzotriazole (2H5M5′V) and Intermediates

| —CH$_2$—C<u>H</u>$_3$ | C<u>H</u>$_2$—CH$_3$ | R$_1$ CHBr—C<u>H</u>$_3$ | —C<u>H</u>B—CH$_3$ | Ar—C<u>H</u>$_3$ | cH a | C=C Ar b Hb | Ha c | <u>H</u> | R$_2$ O ‖ C—C<u>H</u>$_3$ | Aromatic protons |
|---|---|---|---|---|---|---|---|---|---|---|
| 1.30(T) | 2.82(D) | | | 2.30(S) | | | | 11.0(S) | | 7.0 to 8.3 |
| 1.30(T) | 2.82(D) | | | 2.30(s) | | | | | 2.43(s) | 7.0 to 8.3 |
| | | 5.17(D) | 1.98(D) | 2.33(s) | | | | | 2.20 | 6.8 to 7.9 |
| | | | | 2.28(s) | 5.3(D) | 5.56(D) | 6.33(DD) | | 2.40 | 7.0 to 8.0 |

TABLE 1-continued

Chemical Shift Data of $^1$H NMR Spectra of 2(2-Hydroxy-5-Methyl)-5-Vinyl-2H—Benzotriazole (2H5M5'V) and Intermediates

| —CH$_2$—C$\underline{H}_3$ | C$\underline{H}_2$—CH$_3$ | CHBr—C$\underline{H}_3$ R$_1$ | —CH$\underline{B}$—CH$_3$ | Ar—C$\underline{H}_3$ | $\overset{cH}{\underset{Ar}{C}}=\overset{Ha}{\underset{Hb}{C}}$ a | b | c | $\underline{H}$ | $\overset{R_2}{\underset{\underset{C—C\underline{H}_3}{\overset{O}{\|}}}{}}$ | Aromatic protons |
|---|---|---|---|---|---|---|---|---|---|---|
| | | | | 2.35(s) | 5.35(D) | 5.80(D) | 6.84(DD) | 11.0(s) | | 7.0 to 8.1 |

Note: Product of
I: Example (2)
II: Example (1)
III: Example (3)
IV: Example (4)
IV: Example (5)

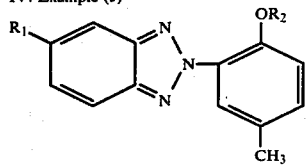

We claim:

1. A homopolymer or copolymer with a vinyl comonomer of a benzotriazole compound having the formula:

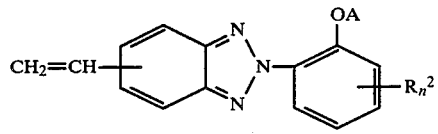

wherein A is hydrogen or acetyl; R$^2$ is C$_{1-4}$ alkyl; and n is 1 or 2 and when n is 2, said R$^2$ radicals may be the same or different.

2. The copolymer of claim 1, wherein the amount of said vinyl benzotriazole compound in the copolymer is in the range of 0.01 to 70 wt%.

* * * * *